(12) United States Patent
Nishina et al.

(10) Patent No.: US 6,324,892 B1
(45) Date of Patent: Dec. 4, 2001

(54) MULTI-GAS ANALYSIS SYSTEM FOR ANALYZING HIGH-PURITY GASES

(75) Inventors: Akira Nishina; Tsutomu Kikuchi; Makoto Tanaka; Hidetoshi Yoshida; Tetsuya Kimijima, all of Tokyo (JP)

(73) Assignee: Nippon Sanso Corporation, Tokyo (JP)

( * ) Notice: Subject to any disclaimer, the term of this patent is extended or adjusted under 35 U.S.C. 154(b) by 0 days.

(21) Appl. No.: 09/445,398

(22) PCT Filed: Apr. 8, 1999

(86) PCT No.: PCT/JP99/01858

§ 371 Date: Dec. 7, 1999

§ 102(e) Date: Dec. 7, 1999

(87) PCT Pub. No.: WO99/53307

PCT Pub. Date: Oct. 21, 1999

(30) Foreign Application Priority Data

Apr. 9, 1998 (JP) .................................................. 10-097971

(51) Int. Cl.[7] ............................ G01N 3/04; G01N 27/62; G01N 30/72; H01J 49/02
(52) U.S. Cl. ................................ 73/23.2; 73/23.37; 73/40
(58) Field of Search ................................. 73/23.2, 23.37, 73/40

(56) References Cited

U.S. PATENT DOCUMENTS 5,823,044 * 10/1998 Logothetis et al. .................... 73/23.2

FOREIGN PATENT DOCUMENTS

| 63-139228 | * 6/1988 | (JP) | ........................................ 73/23.2 |
| 4-80631 | * 3/1992 | (JP) | ........................................ 73/23.2 |
| 6-34616 | 2/1994 | (JP) . | |
| 9-184793 | 7/1997 | (JP) . | |

* cited by examiner

*Primary Examiner*—Daniel S. Larkin
(74) *Attorney, Agent, or Firm*—Armstrong, Westerman, Hattori, McLeland & Naughton, LLP

(57) ABSTRACT

There are provided an apparatus for analyzing gases and a gas analyzing method which can securely detect presence and absence of leakage in a short time and which can carry out analyses successively, safely and accurately in a stable state. The apparatus for analyzing gases is provided with sample gas introducing systems (1 to 5) for introducing a plurality of sample gases selectively, and analyzers (6, 10 and 14), and also has means (9) for monitoring, when a sample gas under determination is changed over to another sample gas, change in the concentration of the sample gas component introduced before the change over.

11 Claims, 5 Drawing Sheets

MULTI-GAS ANALYSIS SYSTEM FOR ANALYZING HIGH-PURITY GASES

TECHNICAL FIELD

The present invention relates to an apparatus for analyzing gases, more particularly to an apparatus for analyzing gases for carrying out safely and accurately monitoring and analysis of gases successively on the spot in plants and the like handling a plurality of gases.

BACKGROUND ART

Gases employed in the semiconductor industries are required to have high purity levels, and also sensitive monitoring and analytical techniques, not of the laboratory level, but of the level employable on the spot, have been strongly desired. Meanwhile, gases are required to have guaranteed levels of as high as from the sub ppm levels to the 10-1 digit ppb levels, and the conventional gas chromatographic analyses are being replaced by analyses using sensitive mass spectrometers or gas chromatograph mass spectrometers. Particularly, among the mass spectrometers, there are recently an increasing number of atmospheric pressure ionization mass spectrometers which carry out ionization under atmospheric pressure to enable sensitive determination.

However, since mass spectrometers and gas chromatograph mass spectrometers are expensive, installation of a plurality of such analyzers to cope with a plurality of gases, respectively, for continuous monitoring results in tremendous costs. Further, since installation of a plurality of analyzers is not preferred either on the standpoint of space saving, a multi-gas analysis system which is directed to analyses of a plurality of gases using one analyzer is desired.

To describe the multi-gas analysis system, the system has one main analyzer and a gas selector installed on the upstream side of the analyzer. Thus, a gas is selected and introduced to the analyzer, and after completion of a determination of the gas, valves are changed over to select another gas species to be analyzed for determination. Although the gases cannot be analyzed continuously due to change-over operations, if the change-over operation is repeated at short intervals, the gases can be analyzed substantially continuously. Consequently, a plurality of gas species can be analyzed by a single analyzer main body, leading to a reduction in the facility cost and in the analyzer installation area.

As described above, although the multi-gas analysis system enjoys many merits, contamination to be caused by mixing of gases occurs easily compared with the case where analyzers are installed for the analyses of the gases respectively, since various kinds of gases are allowed to flow through the gas selector installed on the upstream side of the analyzer. Particularly, since change-over operation is carried out frequently for a plurality of sample gases at desired intervals, external leakage due to damage or abrasion of valves employed or internal leakage due to damage of valve seats can occur easily to be causative of contamination. For example, depending on the kind of gas causing the internal leakage, measured values of impurity contents in the gas actually in determination are affected by the contamination like external leakage to be a hindrance to accurate analysis. External leakage also causes not only migration of air to contaminate the gas in the piping, but also errors in the analytical values.

However, what should be noted here is that such internal leakage and external leakage should be avoided absolutely for security sake, since they can cause accidents if they occur when highly reactive gases are being analyzed. For example, for the external leakage, security can be maintained by detecting hydrogen as a combustible gas and oxygen using a hydrogen detector, etc. and an oxygen detector, respectively, and by detecting other incombustible gases (nitrogen, argon, helium, etc.) if leaked in large amounts using an oxygen deficiency meter.

However, in the case where hydrogen and oxygen used in electronic industries whose purity levels should be monitored strictly are to be analyzed using the multi-gas analysis system as described above, occurrence of an internal leakage due to damage of a valve seat and the like when the gas is changed over to the other, these two gases are mixed in the system to be liable to cause fires, explosions, etc. In order to avoid such combination of the gases, separate analysis systems should be installed for hydrogen and oxygen respectively. Meanwhile, occurrence of an external leakage in a passage of silane, arsine, etc. which are semiconductor material gases can also cause explosion, so that such leakages should be detected and coped with as soon as possible. However, in the commercially available leakage detectors, there is no suitable one which is satisfactory in response and sensitivity, and which can be utilized as inserted to the gas passage.

It is an objective of the present invention to provide an apparatus and a method for analyzing gases, which ensure detection of presence and absence of leakage in a short time and which enable analyses successively, safely and accurately in a stable state.

DISCLOSURE OF THE INVENTION

The apparatus for analyzing gases according to the present invention has a sample gas introducing system for introducing a plurality of sample gases selectively by change-over operations and an analyzer, and the analyzer is provided with means for monitoring, when a sample gas under determination is changed over to another sample gas, a change in the concentrations of the sample gas component introduced before the change-over.

Meanwhile, this apparatus for analyzing gases is also provided with means for safely stopping analytical operation of the apparatus for analyzing gases when a rate of concentration change of the sample gas component introduced before the change over is not identical to a predetermined rate of concentration change by closing a shut-off valve or purging of a passage with an inert gas such as nitrogen. This means for safely stopping analytical operation of the apparatus for analyzing gases carries out at least either an operation of closing a shut-off valve or an operation of purging of a passage with an inert gas, such as nitrogen.

Further, the analyzer is a mass spectrometer, an atmospheric pressure ionization mass spectrometer, or a combination of a gas chromatograph and such a mass spectrometer. The plurality of sample gases to be determined are at least two kinds selected from nitrogen, argon, hydrogen, helium, and oxygen. Particularly, when the plurality of sample gases are nitrogen, hydrogen, argon, helium, and oxygen, these sample gases are introduced selectively to the detector for analysis in this order. Further, the plurality of sample gases can include at least one of silane, phosphine, arsine, hydrogen selenide, and diborane.

The method for analyzing gases according to the present invention, in analyzing a plurality of sample gases successively by introducing to an analyzer the sample gases selectively by change-over operations, carries out monitoring, when a sample gas under determination is a changed over to another sample gas, change in the concentration of the sample gas component introduced before the change-over; and detecting a presence or an absence of leakage in each section of the analyzer based on the change in the concentration. Particularly, when a sample gas having reactivity is analyzed, an analysis of an inert gas is carried out.

According to the present invention, a presence or an absence of leakage through valves and the like can securely be detected in a short time, enabling analyses of various kinds of sample gases successively, safely, and accurately in a stable state.

BEST MODE FOR CARRYING OUT THE INVENTION

Figure 1:
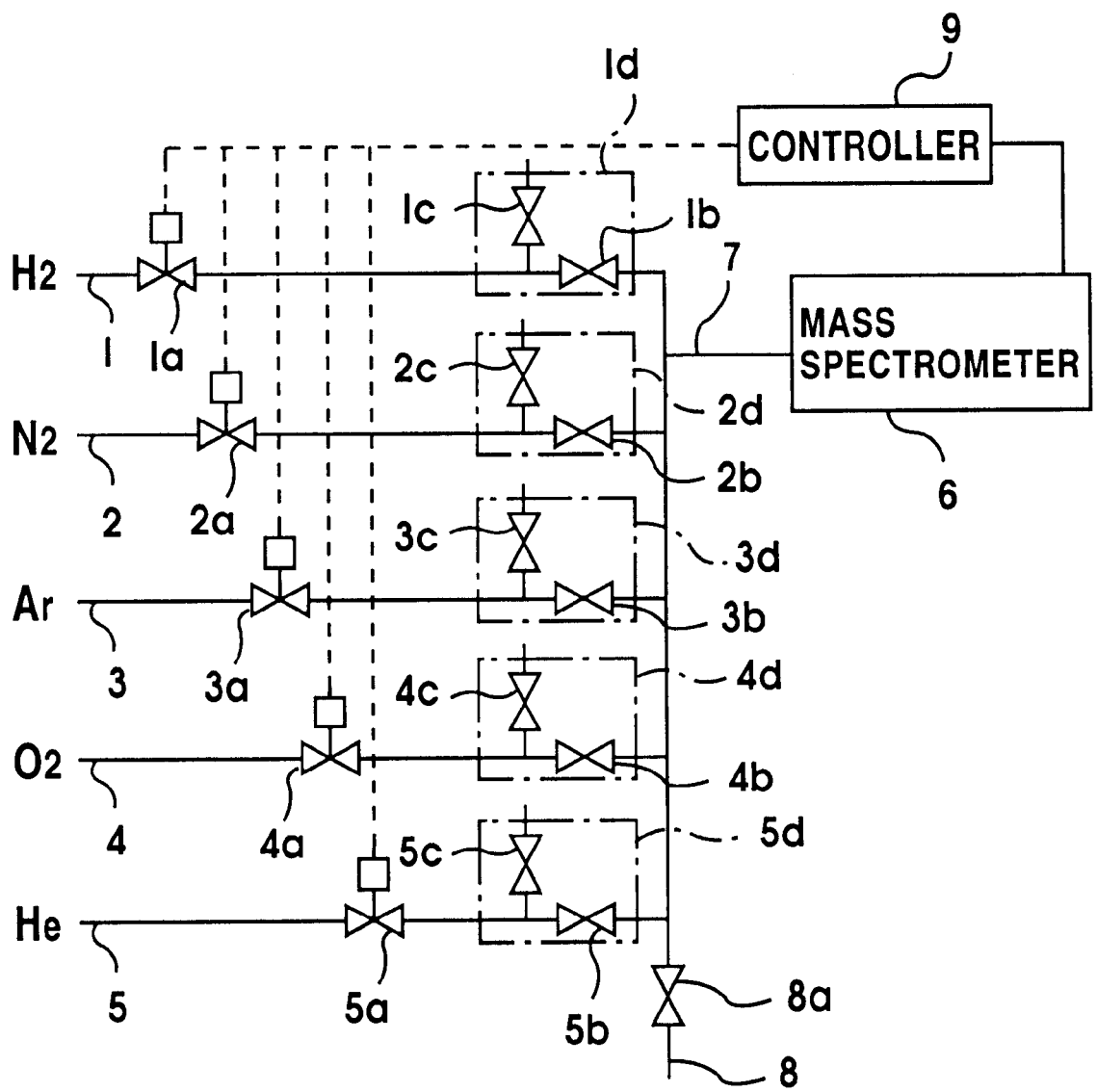
FIG. 1 is a system diagram showing an apparatus for analyzing gases according to one embodiment of the present invention.

FIG. 1 is a system diagram showing an apparatus for analyzing gases according to one embodiment of the present invention in terms of a multi-gas analysis system for analyzing high-purity gases (generally having impurity contents of 10 ppb level or less) for semiconductor industries using an atmospheric pressure ionization mass spectrometer as an analyzer.

This apparatus for analyzing gases, which is directed to analyses of trace impurity contents in five kinds of high-purity gases including hydrogen ($H_2$), nitrogen ($N_2$), argon (Ar), oxygen ($O_2$), and helium (He), contains introduction passages 1, 2, 3, 4, and 5 for introducing the high-purity gases as sample gases; an assay passage 7 for introducing each high-purity gas to an atmospheric pressure ionization mass spectrometer 6; an exhaust passage 8 having an exhaust valve 8a for purging the assay passage 7 when a sample gas is changed over to another sample gas; and a controller 9 which monitors occurrence of leakage and shuts off each introduction passage if any leakage occurs.

The introduction passages 1, 2, 3, 4, and 5 are provided with shut-off valves 1a, 2a, 3a, 4a, and 5a, and selector valves 1d, 2d, 3d, 4d, and 5d which are combinations of assay valves 1b, 2b, 3b, 4b, and 5b and purge valves 1c, 2c, 3c, 4c, and 5c, respectively, and the sample gases are designed to be introduced to the atmospheric pressure ionization mass spectrometer 6 in a predetermined order by inverting the open and closed states of the assay valves and purge valves in predetermined orders.

That is, if the assay valve and the purge valve provided in the introduction passage for the gas to be analyzed are opened and closed respectively, while the assay valves and purge valves in the other introduction passages are closed and opened respectively, this brings about a state where only the desired gas is introduced through the corresponding assay valve to the atmospheric pressure ionization mass spectrometer 6. Meanwhile, with respect to the other gases, by carrying out purging constantly with these gases through the corresponding purge valves, contamination of the high-purity gases to be caused by adsorption and desorption to and from the piping can be minimized, and each gas can constantly be introduced to the analyzer in a high-purity state. Such change-over between the gas species is carried out in a predetermined determination cycle, for example, in a cycle of about thirty minutes, and the high-purity gases are analyzed successively.

In the thus constituted so-called multi-gas analysis system, if the gas species is changed over to another gas species and if the gas introduced before the change-over is determined, a gradual decrease in the concentration of the gas is observed with a decrease of the residual gas. However, if the assay valve is not closed completely to cause leakage of the gas, a decrease in the concentration to a predetermined level is not observed even after a predetermined time.

Figure 2:
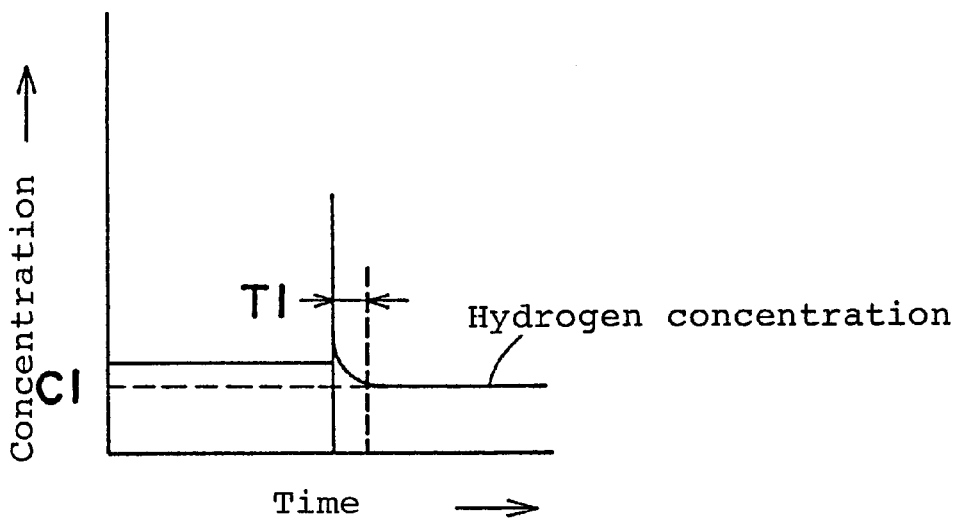
FIG. 2 is a chart showing an example of concentration change under no leakage.
Figure 3:
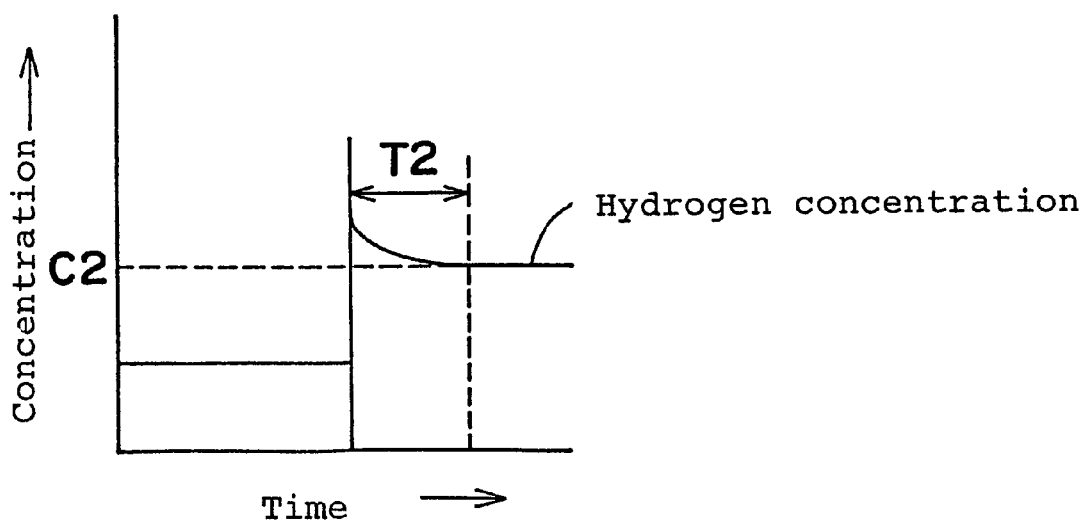
FIG. 3 is a chart showing an example of concentration change under leakage.

For example, in the case where hydrogen in argon is to be determined after determination of nitrogen as an impurity content in hydrogen, when the assay valve 1b for hydrogen introduced before the change-over is fully closed, the hydrogen concentration drops to a predetermined level C1 after a predetermined time T1, as shown in FIG. 2. However, when the assay valve 1b is closed incompletely, the time T2 until the concentration reaches the predetermined level is longer and the concentration C2 is higher compared with the usual case, as shown in FIG. 3.

Accordingly, a presence or an absence of leakage in the assay valve for introducing hydrogen can be detected by monitoring a change in the hydrogen concentration and comparing it with the time and concentration under usual operation, when the analysis of hydrogen is changed over to an analysis of argon. While the same shall apply to combinations of other gases, it is known that the assay sensitivity is influenced greatly by coexistent materials when the atmospheric pressure ionization mass spectrometer is used as the analyzer, and it can occur that impurity contents cannot be detected with high sensitivity depending on the combination of gases. Thus, it is necessary to determine the order of changing over the gases so that the gas before the change-over can be detected with high sensitivity in the gas after the change-over. For example, by carrying out a change-over of gases in the order of nitrogen, hydrogen, argon, helium to oxygen, the major component gas before the change-over can be detected in the major component gas after the change-over.

More specifically, when the sample gas is changed over from nitrogen to hydrogen, nitrogen in hydrogen can be determined by the atmospheric pressure ionization mass spectrometer, whereas when the sample gas is changed over from hydrogen to argon, hydrogen in argon can be determined. It should be noted here that when the sample gas is changed over from helium to oxygen, leakage of helium cannot be detected because helium in oxygen can hardly be determined, but helium per se, if undergoes internal leakage, will not affect measured values and causes no problem in security. Accordingly, a presence or an absence of leakage can also be checked by introducing helium for a predetermined time when a sample gas is changed over to another sample gas.

Further, in the case of an atmospheric pressure ionization mass spectrometer, since helium has the highest ionization potential compared with any gas, all of the other gas species can be detected. This makes it possible to use helium gas in leak inspections when the system is started up or during periodical maintenance work. In addition, even during successive determination, each helium gas determination can be utilized also as confirmation of safety to find a presence or an absence of external leakage.

Figure 4:
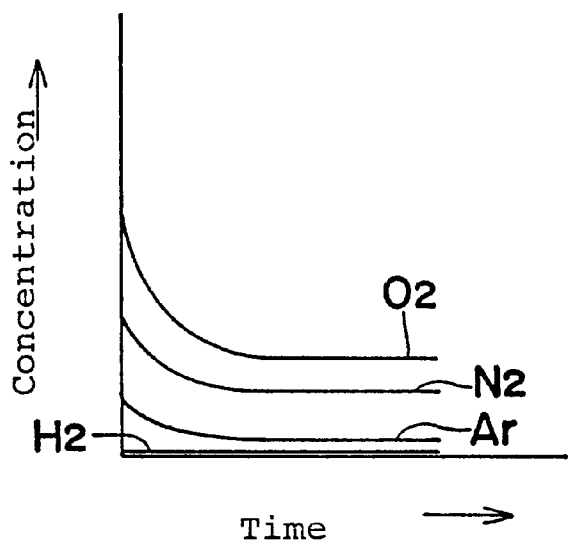
FIG. 4 is a chart showing an example of concentration change in each component under no leakage.
Figure 5:
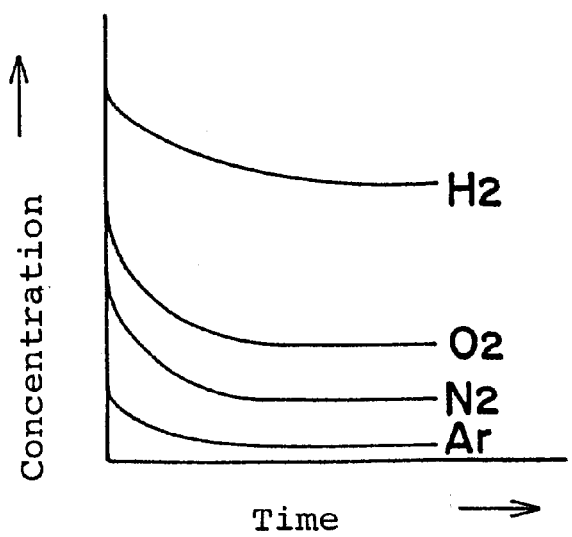
FIG. 5 is a chart showing an example of concentration change under hydrogen leakage.

For example, FIGS. 4 and 5 show examples of changes in the concentrations of hydrogen, nitrogen, argon, and oxygen when helium was measured in the atmospheric pressure ionization mass spectrometer 6 with the assay valves for the gases other than helium being closed. FIG. 4 shows a usual state where there is no leakage in the assay valves, while FIG. 5 shows a state where leakage is occurring in the hydrogen assay valve. As described above, by comparing changes in the concentrations of the gases when helium is analyzed, it is possible to find an occurrence of leakage in the assay valve of the gas having an increased concentration, in this case the hydrogen assay valve. Further, an increase in the concentrations of nitrogen and oxygen proportional to the sensitivity ratio of nitrogen to oxygen=4:1 corresponding to the compositional ratio as air components is judged to be an occurrence of external leakage through fitting and the like in the piping.

In the case of hydrogen leakage, or oxygen leakage, or of migration of the outside air, at least the hydrogen shut-off valve 1a is closed based on a command from the controller 9 so as to avoid the danger of mixing of hydrogen and oxygen to cause combustion or the like. Thus, the danger of combustion and the like can be avoided to allow the analyzer to be safely stopped.

Meanwhile, all of the shut-off valves may be closed based on a command from the controller 9, or the shut-off valves for combustible and combustion assisting gases, such as hydrogen and oxygen, other than the inert gases may be adapted to be closed. Further, only an assay valve for an inert gas such as nitrogen and argon, e.g., only the nitrogen assay valve 2b is opened, and also the valve 8a of the exhaust passage 8 is opened to introduce nitrogen gas into the system of the assay passage 7 containing an assay valve connecting sections and the like, so that the combustible gas and the like may be purged out.

As described above, in the case where a mass spectrometer which carries out analyses with high sensitivity and with high response speed is used for analyzing high-purity gases, the analyzer per se can be utilized as a high-speed and high-sensitivity leakage detector, requiring no extra detectors. Further, by designing that the shut-off valves may be closed or that the inside of the system is purged with an inert gas, when any leakage is detected, security can fully be enhanced, and unattended monitoring on the spot can be performed safely.

Therefore, when four species of gases are to be analyzed in the above embodiment, for example, the gases other than argon are to be determined, nitrogen, hydrogen, helium, and oxygen are determined in this order; whereas the gases other than helium are to be determined, nitrogen, hydrogen, argon, and oxygen are determined in this order.

Meanwhile, while three species of gases can also be analyzed likewise, when gases other than argon, and helium are to be determined, nitrogen, hydrogen and oxygen are determined in this order. However, this case involves a dangerous change-over from a combustible gas to a combustion assisting gas, so that an inert gas, nitrogen, is interposed between hydrogen and oxygen in the above order, and nitrogen, hydrogen, nitrogen, and oxygen are determined in this order. That is, the determination of an inert gas to be analyzed is interposed before and after determination of a combustible gas and that of a combustion assisting gas and between them. In this case, in the change-over from nitrogen to oxygen, although it has been difficult in the ordinary atmospheric pressure ionization mass spectrometer to monitor the change in the concentration of nitrogen in oxygen, it can be achieved by using a special atmospheric pressure ionization mass spectrometer having a twin-compartment ion chamber.

Detection of leakage can be carried out in the same manner as described above. For example, when the sample gas is changed over from argon to hydrogen, a presence or an absence of leakage can be detected by monitoring a change in the concentration of argon in hydrogen, and further shutting off of gases using the shut-off valves and purging in the system can be carried out in the same manner as described above.

Figure 6:
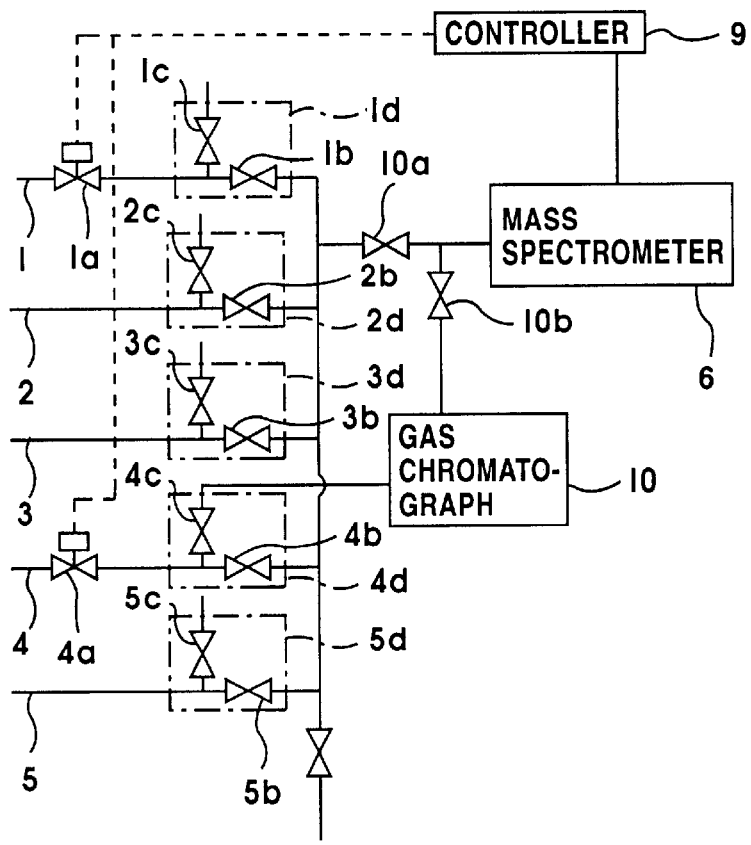
FIG. 6 is a system diagram showing an example of an analyzer having a combination of a gas chromatograph and an atmospheric pressure ionization mass spectrometer.

FIG. 6 is a system diagram showing an embodiment where impurity contents other than moisture in oxygen are assayed using an atmospheric pressure ionization mass spectrometer 6 via a gas chromatograph 10. In this embodiment, introduction passages 2, 3, and 5 for inert gases including nitrogen which are free from the fear of combustion and the like are not provided with shutoff valves, but only the introduction passages 1 and 4 for hydrogen and oxygen are provided with shut-off valves 1a and 4a, respectively. When any leakage occurs, the shut-off valves 1a and 4a of these two passages are designed to be closed based on a command from a controller 9. Further, change-over between the passage via the gas chromatograph 10 and the ordinary passage is carried out by opening and closing valves 10a and 10b. Since the other constituents are the same as shown in FIG. 1, they are affixed with the same reference numbers, respectively, and detailed description of them will be omitted.

Figure 7:
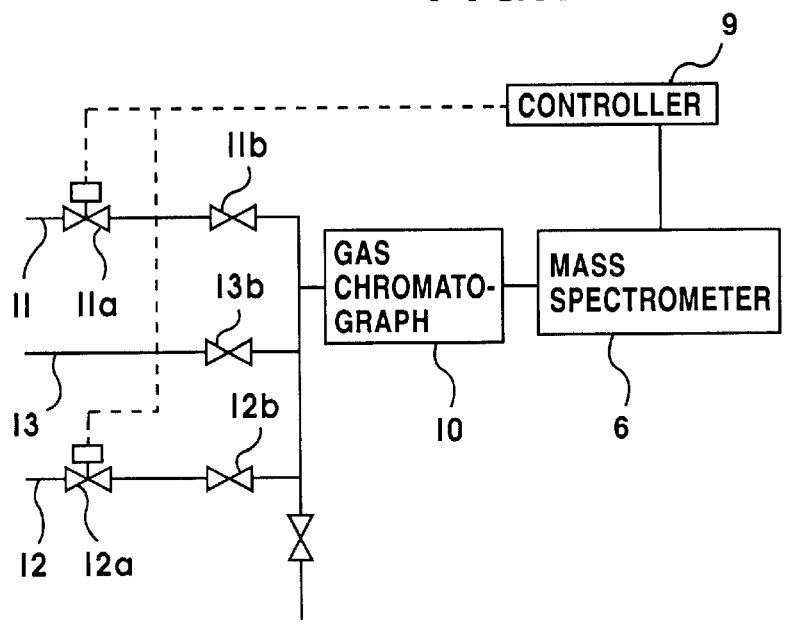
FIG. 7 is a system diagram showing an example of an analyzer for analyzing a semiconductor material gas.

FIG. 7 shows an embodiment where determination is carried out using an atmospheric pressure ionization mass spectrometer 6 combined in series with a gas chromatograph 10 as an analyzer for analyzing semiconductor material gases, for example, two kinds of gases, i.e., silane and arsine. Particularly, semiconductor material gases such as silane, phosphine, arsine, hydrogen selenide and diborane are causative of explosion or fires through reaction with air components remaining in the piping and the like, so that the piping should fully be purged when the gas to be determined is to be changed over to the other, and after sufficient purging of the piping, the channel is changed over to the gas to be determined.

Accordingly, in this case, purging of the system is carried out by introducing an inert gas, such as helium, argon, and nitrogen, which give rise to no problem in determination, from an introduction passage 13 between the analysis of silane from an introduction passage 11 and the analysis of arsine from an introduction passage 12, and also a change in the concentration of silane or arsine in the inert gas is monitored, followed by changing over of the gas to be determined to the other gas after confirmation of detection of no silane or arsine. If silane or arsine is detected even after passage of a predetermined time, and if the peak is not reduced even after repetition of the measurement several times, such a case is judged to be a leakage present in the assay valves 11b and 12b provided in the passages 11 and 12, respectively, and the shut-off valves 11a and 12a provided in these passages 11 and 12 are adapted to be closed based on a command from a controller 9. The reference number 13b denotes a purge valve.

Incidentally, while the kind and combination of gases to be analyzed can be selected as desired, when hydrogen and oxygen having reactivity or semiconductor material gases are to be analyzed, the order of selecting the gases should be decided such that analysis of inert gas may be interposed before, and after analyses of such gases. Further, as the analyzer per se, those of various constitution may be used so long as they can detect concentration changes caused by leakage.

Figure 8:
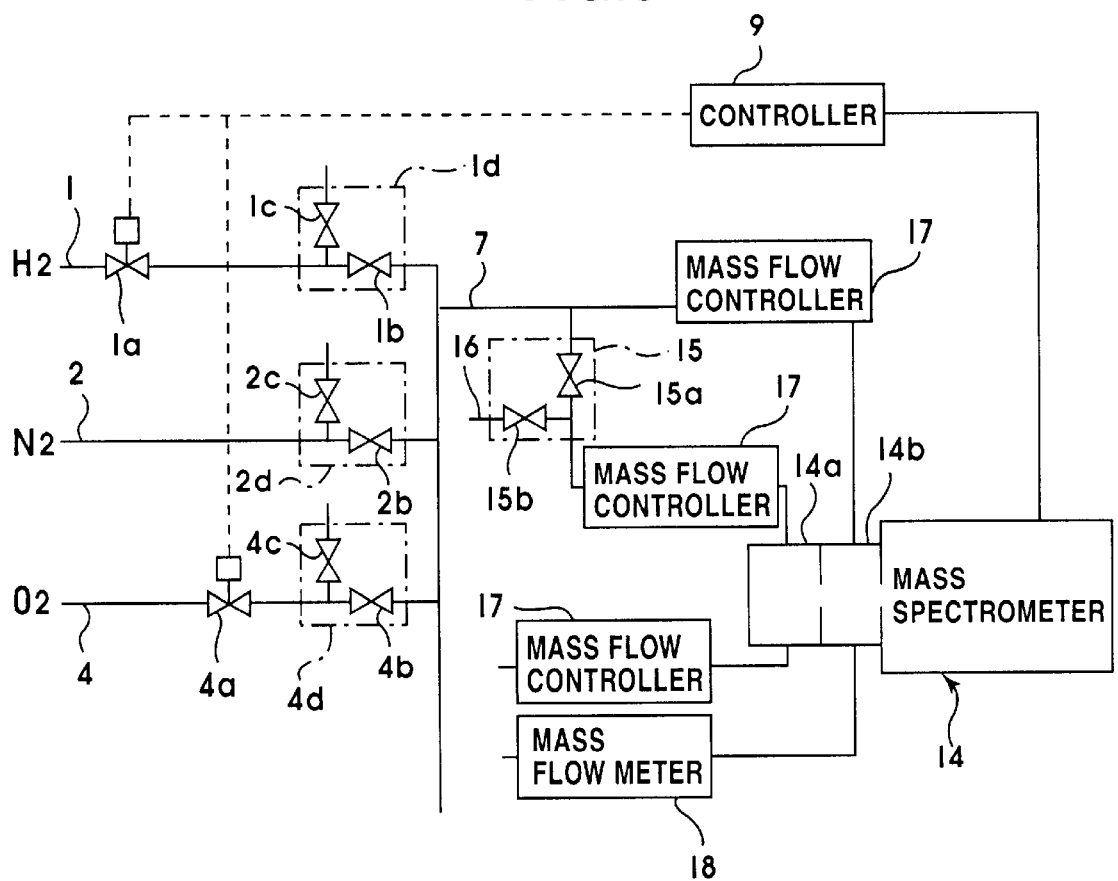
FIG. 8 is a system diagram for explaining operations of changing over a sample gas to another sample gas in the case where three sample gases, i.e., hydrogen, nitrogen, and oxygen, are to be measured.

Next, there is described a test example for analyzing three kinds of gases, i.e. hydrogen, nitrogen, and oxygen, using the analyzer having the constitution as shown in FIG. 8.

Since the gas species include hydrogen and oxygen, determination of nitrogen is interposed before, and after determinations of these two gas species to determine nitrogen, hydrogen, nitrogen, and oxygen in this order.

Further, in order to monitor a change in the concentration of the sample gas component before the change-over, concentrations of nitrogen in hydrogen, hydrogen in nitrogen, nitrogen in oxygen, and oxygen in nitrogen should be determined.

Since it is difficult theoretically to determine nitrogen in oxygen in the ordinary atmospheric pressure ionization mass spectrometer, an atmospheric pressure ionization mass spectrometer (Hitachi Tokyo Electronics) 14 having a two-step ion source chambers 14a and 14b formed by dividing an ion source section into two compartments was used.

First, a nitrogen assay valve 2b and an assay valve 15a of a gas selector valve 15 were opened to introduce nitrogen into the ion source chambers 14a and 14b and carry out analysis. Next, the assay valve 2b and a hydrogen assay valve 1b were closed and opened, respectively, to change the gas from nitrogen to hydrogen. Then, nitrogen in hydrogen was determined, and after confirmation of the phenomena that the nitrogen content is decreasing at a normal rate, determination of hydrogen was carried out. Subsequently, the assay valve 1b and the assay valve 2b were closed and opened respectively to change over the gas again to nitrogen, and upon confirmation of reduction of hydrogen in nitrogen at the normal rate, the assay valve 2b and an oxygen assay valve 4b were closed and opened respectively to change over the gas to oxygen.

Then, the assay valve 15a and an inlet valve 15b were also closed and opened respectively to introduce a mixed gas (0.1 to 0.01%) of argon and hydrogen to the first ion source chamber 14a from the passage 16, while oxygen was introduced to the second ion source chamber 14b. This is a means for determining nitrogen in oxygen and is directed to a realization of the determination of nitrogen concentration in oxygen by supplying the mixed gas of argon, and hydrogen to the first ion source chamber 14a to effect conversion of the reaction of oxygen in the second ion source chamber 14b to a proton transfer reaction, enabling the determination of the reduction rate of nitrogen. Thus, the rate of replacement of nitrogen with oxygen was determined.

Finally, in order to select nitrogen again, the assay valve 4b and the assay valve 2b were closed and opened respectively, and also the inlet valve 15b and the assay valve 15a were closed and opened respectively, to supply nitrogen again to the first and second ion source chambers 14a and 14b and determine the oxygen concentration in nitrogen. After confirmation of the reduction of oxygen, nitrogen was determined.

As a result, it was found that nitrogen in hydrogen, hydrogen in nitrogen, nitrogen in oxygen and oxygen in nitrogen were decreased to 5 ppb or less in five, ten, seven and five minutes, respectively. A reduction time greater than the above levels and no reduction at all in a predetermined time are detected as an occurrence of leakage or damage of the valves. In the above change-over operations, all the major component gases were reduced in predetermined times, so that it was found that no internal leakage attributed to valve damage and the like was present.

Incidentally, the reference numbers 17 and 18 denote mass flow controller and mass flowmeter, respectively.

What is claimed is:

1. An apparatus for analyzing gases comprising a sample gas introducing system for introducing a plurality of sample gases selectively by change-over operations and an analyzer, the analyzer being provided with means for monitoring, when a sample gas under determination is changed over to another sample gas, a change in the concentration of the sample gas component introduced before the change-over.

2. The apparatus for analyzing gases according to claim 1, further comprising means for safely stopping analytical operation of the apparatus for analyzing gases when a rate of concentration change of the sample gas component introduced before the change over is not identical to a predetermined rate of concentration change.

3. The apparatus for analyzing gases according to claim 2, wherein the means for safely stopping analytical operation is a means for carrying out at least either an operation of closing a shut-off valve or an operation of purging of a passage with an inert gas.

4. The apparatus for analyzing gases according to claim 3, wherein the inert gas is nitrogen.

5. The apparatus for analyzing gases according to claim 2, wherein the plurality of sample gases include at least one of silane, phosphine, arsine, hydrogen selenide, and diborane.

6. The apparatus for analyzing gases according to claim 1, wherein the analyzer is a mass spectrometer, or a combination of a gas chromatograph and a mass spectrometer.

7. The apparatus for analyzing gases according to claim 1, wherein the analyzer is an atmospheric pressure ionization mass spectrometer or a combination of a gas chromatograph and an atmospheric pressure ionization mass spectrometer.

8. The apparatus for analyzing gases according to claim 1, wherein the plurality of sample gases are at least two kinds selected from nitrogen, argon, hydrogen, helium, and oxygen.

9. The apparatus for analyzing gases according to claim 1, wherein the plurality of sample gases are nitrogen, hydrogen, argon, helium, and oxygen, and these sample gases are introduced selectively to the analyzer in this order.

10. A method for analyzing gases, in analyzing a plurality of sample gases successively by introducing to an analyzer the sample gases selectively by change-over operations, the method comprising:

monitoring, when a sample gas under determination is changed over to another sample gas, a change in the concentration of the sample gas component introduced before the change-over; and detecting a presence or an absence of leakage in each section of the analyzer based on the change in the concentration.

11. The method for analyzing gases according to claim 10, wherein an analysis of a sample gas having reactivity is followed by an analysis of an inert gas.

* * * * *